United States Patent
Klosowski et al.

(10) Patent No.: US 10,208,165 B2
(45) Date of Patent: Feb. 19, 2019

(54) CURABLE SILICONE COMPOSITIONS THAT CURE THROUGH COMMAND CATALYSIS

(71) Applicants: Jerome Klosowski, Bay City, MI (US); Timothy Krytenberg, Vancouver, WA (US); Larry D. Vockler, Vancouver, WA (US)

(72) Inventors: Jerome Klosowski, Bay City, MI (US); Timothy Krytenberg, Vancouver, WA (US); Larry D. Vockler, Vancouver, WA (US)

( * ) Notice: Subject to any disclaimer, the term of this patent is extended or adjusted under 35 U.S.C. 154(b) by 116 days.

(21) Appl. No.: 15/144,868

(22) Filed: May 3, 2016

(65) Prior Publication Data

US 2017/0321013 A1 Nov. 9, 2017

(51) Int. Cl.
| | | |
|---|---|---|
| C08G 77/08 | (2006.01) | |
| C08G 77/04 | (2006.01) | |
| C08K 3/36 | (2006.01) | |
| C08K 3/26 | (2006.01) | |
| C09D 183/04 | (2006.01) | |
| C09D 7/61 | (2018.01) | |
| C07F 7/00 | (2006.01) | |
| C07F 7/22 | (2006.01) | |
| C08K 3/22 | (2006.01) | |

(52) U.S. Cl.
CPC .............. *C08G 77/08* (2013.01); *C07F 7/003* (2013.01); *C07F 7/226* (2013.01); *C08G 77/04* (2013.01); *C08K 3/26* (2013.01); *C08K 3/36* (2013.01); *C09D 7/61* (2018.01); *C09D 183/04* (2013.01); *C08K 2003/2241* (2013.01); *C08K 2003/265* (2013.01)

(58) Field of Classification Search
CPC ....................................................... C08G 77/08
USPC .......................................................... 524/425
See application file for complete search history.

(56) References Cited

U.S. PATENT DOCUMENTS

| | | | | |
|---|---|---|---|---|
| 5,827,922 | A * | 10/1998 | Chen .................... | C08K 5/5415 524/837 |
| 2010/0040570 | A1 * | 2/2010 | Falk ....................... | A61K 8/585 424/70.1 |
| 2013/0122314 | A1 * | 5/2013 | Ou ......................... | A61L 29/085 428/429 |
| 2013/0165619 | A1 * | 6/2013 | Meyer Zu Berstenhorst ............. | C08G 18/246 528/49 |

* cited by examiner

*Primary Examiner* — Doris L Lee

(57) ABSTRACT

Inhibited tin or titanate catalysts are used in condensation cures of silicone materials. Such catalysts are command cure systems with long open pot life, yet have relatively fast cure when the cure mechanism is triggered. This combines the advantages of the inhibited addition cure systems (command cure) with the advantages of the condensation cure systems (lower cost).

6 Claims, No Drawings

CURABLE SILICONE COMPOSITIONS THAT CURE THROUGH COMMAND CATALYSIS

BACKGROUND OF THE INVENTION

Curable silicone compositions have been known since the 1940's and been used in a variety of end use applications. The silicone polymers are silanol end-blocked and are mixed with alkoxy silanes for crosslinking and cure activities. Typically, these materials have condensation cures, that is, they curs through condensation of the silanol end groups on the silicone polymer with water as the by-product. they are typically enclosed in air tight containers along with condensation catalysts to prevent the premature curing, because once removed from the container, for example, a tube, they begin to cure. Also, in some end uses, the materials are used in coating and dipping operations where the coatings are used in open vessels and they therefore tend to increase in viscosity, i.e. premature cure.

Thus, for any end use application that requires preparation time using the silicone compositions, it would be valuable to provide a delay in the cure of the silicone compositions and thus, it is desirable to use a cure that can be taken on command (command cure). In the field of coatings for substrates such as glass or other applications, there has been an increasing need to have a command cure.

Some existing condensation catalysts, like tin and titanate compounds, cure so well at room temperature that they have very short use times. These catalysts are mixed as a system wherein the catalyst and crosslinker are mixed by an operator immediately prior to use. The mixture is then applied shortly after mixing, resulting in time-related restrictions on the manufacturing processes. Such fast cure systems typically have a very short open pot life.

Many room temperature vulcanizing (RTV) silicone products, such as sealants, utilize condensation curing mechanisms to facilitate rapid polymer cross-linking. These mechanisms can be generalized as reactions between a silanol terminated polymer (typically polydimethylsiloxane) and a multi-functional cross-linking agent such as methyltrimethoxysilane with the use of a catalyst:

Further cross-linking can be obtained by hydrolyzing the remaining functional groups with ambient moisture, which can further react with any remaining cross-linking agent:

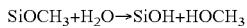

These reactions are often catalyzed by metal complexes, most commonly tin and titanate complexes such as dibutyltindilaurate and tetrabutyltitanate. These reactions are very quick, usually limited only by the amount of ambient moisture available for hydrolysis and as such there is a desire to inhibit the cure rate to give more control over a product. Conventionai tin catalysts also never deactivate, and remain in the product to catalyze the reversal of the aforementioned condensation reactions:

These conventional catalysts are less stable and can be easily compromised in the presence of heat, fire or weather. Such a reaction tends to occur in the presence of excess moisture and heat. This is due to the non-active ligands present on the metal catalyst, for example the butyl groups on dibutyltindilaurate. Since these alkyl groups never react, they keep the tin complexes soluble in the siloxane which can lead to tin-catalyzed polymer cleavage.

Some materials, like thin film silicone coatings, achieve a longer pot life using inhibited platinum catalysts, encapsulated platinum catalysts, or very slow cure forms of the precious metal catalysts to achieve the command cure in silicone, known as "addition cure" chemistry. Addition cure refers to the hydrosilyation reaction between a hydride functional silicone and an unsaturated moiety. The inhibited cures with these types of ingredients are much more expensive than the silanol ended polymers used in condensation curing systems, thus making them more expensive products.

It is desirable to have a system where the materials can be open to the air, applied to the surface of a substrate and then the cure mechanism is triggered, while using low-cost products. In many situations, a command cure, which allows for a longer pot life, that could be achieved at relatively low cost, is desired.

The present invention demonstrates that inhibited tin or titanate catalysts can be used in condensation cures and can be command cure systems with long open pot life, yet have relatively fast cure when the cure mechanism is triggered. This combines the advantages of the inhibited addition cure systems (command cure) with the advantages of the condensation cure systems (lower cost). In addition, the inhibited catalyst is completely deactivated which provides for a final product that is more heat, fire, and weather stable, and is not biologically active. Another benefit of a command cure in a condensation system is that adhesion is typically easier to achieve in condensation systems and thus a command curs with lower cost also has the potential to achieve better adhesion.

By inhibiting the reactivity of conventional condensation cure catalysts such as tin or titanate compounds, the catalysts may remain in fully formulated materials without showing catalytic activity, thereby contributing to a longer pot life. Such catalysts may be inhibited using alcohols, mercaptans, and/or chelates.

This technology may be applied to a variety of products including silicone, urethanes (coatings, sealants, plastics), and polyesters (used in urethanes).

The present invention may also fee used for coatings for glass and other applications, such as sealants. Embodiments of the present invention may be used with roof tiles, siding, sealants (construction, marine, home), adhesives, concrete coatings, glass coatings, auto air bags, gaskets, hose & tubing, injection molding, pressure-sensitive release coatings, RTV silicones, and fabric coatings.

Command catalysts of inhibited tin and titanate can be made by any of the techniques known to chemists in the industry. One such technique is a ligand exchange. An example is $Bu_2SnCl_2 + 2RSH \longrightarrow Bu_2Sn(SR)_2 + HCl$. Another is $Bu_2Sn(OAc)_2 + 2RSH \longrightarrow Bu_2Sn(SR)_2 + 2HOAc$. Yet another is $Sn(OAC)_4 + 4RSH \longrightarrow Sn(SR)_4 + 4HOAc$. Another example is $Ti(OPr)_4 + HN(CH_2CH_2OH)_3 \longrightarrow Ti(NCH_2CH_2O) + 4HOPr$. In each case the leaving groups, if it is more volatile, can be stripped out, or if acidic, can be captured by an acceptor to make a salt that can be filtered out. These are but a few examples of the techniques common to the industry used, to make the catalysts used in these formulations.

THE INVENTION

Thus, what is disclosed and claimed herein in one embodiment, is a composition of Matter. The composition of matter is selected from the group consisting of a tin compound selected from the group of formulae consisting of $Sn(Y)_n(X)_{4-n}$ wherein Y is a sulfide group with the general formula RS⁻ wherein R is a linear, branched or cyclic alkyl group having 1 to 20 carbon atoms or an aryl group containing 6 to 20 carbon atoms, X is selected from a linear, branched, or cyclic alkoxy group, enoloxy group, or carboxylate ester having 1 to 20 carbon atoms, n has a value of 1, 2, 3, or and 4, and 1≤n≤4.

$Sn(Y)_n(X)_{2-n}$ wherein Y is a sulfide polydentate ligand, X is a linear, branched, or cyclic alkoxy group, an amine, or a carboxylate ester, having 1 to 20 carbon atoms, wherein 1≤n≤2.

Sn(Y)(X) wherein Y is a sulfide tridentate ligand with the general formula ⁻SARA wherein R is a linear, branched or cyclic alkyl group having 1 to 20 carbon atoms and wherein A is S⁻, O⁻, or COO⁻, X is a linear, branched or cyclic alkoxy, enoloxy, or carboxylate ester having 1 to 20 carbons atoms; a titanate compound selected from the formulae consisting of Ti(X) wherein X is a polydentate ligand with the general formula ARARARA wherein R is a linear, branched or cyclic alkyl group having 1 to 20 carbon atoms and A is selected from N, O⁻, or COO⁻.

In the case of the formula $Sn(Y)_n(X)_{4-n}$, n has a value of 1, 2, 3, or 4. The preferred value for n is 2 or 4. Y is a sulfide group with the general formula RS⁻ wherein R is a linear, branched, or cyclic alkyl group having 1 to 20 carbon atoms, or an aryl group containing 6 to 20 carbon atoms. X is a linear, branched, or cyclic alkoxy, enoloxy, or carboxylate ester having 1 to 20 carbon atoms.

Examples of Y are n-octylmercaptide, 2-ethylhexylmercaptide, trimethoxysilylpropylmercaptide, triethoxysilyl-proplmercaptide, dodecylmercaptide, cyclopentylmercaptide, phenylethylmercaptide and the preferred groups are trimethoxysiylpropylmercaptide and dodecylmercaptide. Examples of X are methoxy, ethoxy, octoxy, acetylacetonate, acetate, ethylhexanoate, dodecanoate and the most preferred groups are dodecanoate and acetylacetonate.

In the case of Sn(Y)(X), Y is a sulfide tridentate ligand having the general formula ⁻SRARA wherein R is a linear, branched or cyclic alkyl group having 1 to 20 carbon atoms and A is S⁻, O⁻, or COO⁻. X is a linear, branched or cyclic alkoxy, enoloxy, or carboxylate ester having 1 to 20 carbon atoms. Y can be, for example, thioglycerol. Some examples of X are methoxy, ethoxy, octoxy, acetylacetonate, acetate, ethylhexanoate, dodecanoate and the most preferred groups are dodecanoate or acetylacetonate.

This invention also deals with another embodiment which is a composition of matter comprising (A.) a silicone composition that cures through silanol condensation reactions and (B.) a command cure catalyst, wherein said command cure catalyst is selected from the group comprising:

$Sn(R)_2(Y)_2$ wherein R is a linear, branched or cyclic alkyl group containing 1 to 20 carbon atoms, Y is a sulfide group having the general formula R¹S⁻ wherein R¹ is a linear, branched or cyclic alkyl group having 1 to 20 carbon atoms or an aryl group having 6 to 20 carbon atoms.

$Sn(Y)_n(X)_{4-n}$ wherein Y is a sulfide group with the general formula RS⁻ is a linear, branched or cyclic alkyl group having 1 to 20 carbon atoms or an aryl group containing 6 to 20 carton atoms, X is selected from an linear, branched, or cyclic alkoxy group, an enoloxy group, or a carboxylate ester having 1 to 20 carbon atoms, n has a value of 1, 2, 3, or 4, and 1≤n≤4.

$Sn(Y)_n(X)_{2-n}$ wherein Y is a sulfide polydentate ligand, X is a linear, branched, or cyclic alkoxy group, an amine, or a carboxylate ester, having 1 to 20 carbon, atoms, wherein 1≤n≤2.

Sn(Y)(X) wherein Y is a sulfide tridentate ligand with the general formula ⁻SARA wherein R is a linear, branched or cyclic alkyl group having 1 to 20 carbon atoms and wherein A is S⁻, O⁻, or COO⁻, X is a linear, branched or cyclic alkoxy, enoloxy, or carboxylate ester having 1 to 20 carbons atoms; a titanate compound selected from the formulae consisting of Ti(X) wherein X is a polydentate ligand with the general formula ARARARA wherein is a linear, branched or cyclic alkyl group having 1 to 20 carbon atoms and A is selected from N, O⁻, or COO⁻.

In the case of the formula $Sn(R)_2(Y)_2$, examples of R and R¹ are butyl, methyl, ethyl, propyl, octyl, and phenyl, with the preferred groups being butyl and methyl, Y is selected from n-octylmercaptide, 2-etylhexylmercaptide, trimethoxysilylpropylmercaptide, triethoxy-silylpropylmercaptide, dodecylmercaptide, cyclopentyl-mercaptide, phenylethylmercaptide and the preferred groups are trimethoxysilyl-propylmercaptide and dodecylmercaptide.

In a further embodiment, there is a method of providing a curable silicone composition that cures through silanol condensation reactions. The method comprises providing the silicone composition; providing a command cure catalyst for the silicone composition; mixing a predetermined amount of the silicone composition and a predetermined amount of the command cure catalyst together, wherein the command cure catalyst is selected front the group consisting of a $Sn(R)_2(Y)_2$ wherein R is a linear, branched or cyclic alkyl group containing 1 to 20 carbon atoms, Y is a sulfide group having the general formula R¹S⁻ wherein R¹ is a linear, branched or cyclic alkyl group having 1 to 20 carbon atoms or an aryl group having 6 to 20 carbon atoms.

$Sn(Y)_n(X)_{4-n}$ wherein Y is a sulfide group with the general formula RS⁻ is a linear, branched or cyclic alkyl group having 1 to 20 carbon atoms or an aryl group containing 6 to 20 carbon atoms, X is selected from an linear, branched, or cyclic alkoxy group, an enoloxy group, or a carboxylate ester having 1 to 20 carbon atoms, n has a value of 1, 2, 3, or 4, and 1≤n≤4.

$Sn(Y)_n(X)_{2-n}$ wherein Y is a sulfide; polydentate ligand, X is a linear, branched, or cyclic alkoxy group, an amine, or a carboxylate ester, having 1 to 20 carbon atoms, wherein 1≤n≤2.

Sn(Y)(X) wherein Y is a sulfide tridentate ligand with the general formula ⁻SARA wherein R is a linear, branched or cyclic alkyl group having 1 to 20 carbon atoms and wherein A is S⁻, O⁻, or COO⁻, X is a linear, branched or cyclic alkoxy, enoloxy, or carboxylate ester having 1 to 20 carbons atoms; a titanate compound selected from the formulae consisting of Ti(X) wherein X is a polydentate ligand with the general formula ARARARA wherein R is a linear, branched or cyclic alkyl group having 1 to 20 carbon atoms and A is selected from N, O⁻, or COO⁻.

In still another embodiment, there is a method of curing a silicone composition that cures through silanol condensation reactions, the method comprising providing the silicone composition providing a command cure catalyst for the silicone composition; mixing a predetermined amount of the silicone composition and a predetermined amount of the command cure catalyst together, wherein the command cure catalyst is selected from the group consisting of a tin compound selected from the group of formulae consisting of Sn(R)$_2$(Y)$_2$ wherein R is a linear, branched or cyclic alkyl group containing 1 to 20 carbon atoms, Y is a sulfide group having the general formula R$^1$S$^-$ wherein R$^1$ is a linear, branched or cyclic alkyl group having 1 to 20 carbon atoms or an aryl group having 8 to 20 carbon atoms.

Sn(Y)$_n$(X)$_{4-n}$ wherein Y is a sulfide group with the general formula RS$^-$ is a linear, branched or cyclic alkyl group having 1 to 20 carbon atoms or an aryl group containing 6 to 20 carbon atoms, X is selected from an linear, branched, or cyclic alkoxy group, an enoloxy group, or a carboxylate ester having 1 to 20 carbon atoms, n has a value of 1, 2, 3, or 4, and 1≤n≤4.

Sn(Y)$_n$(X)$_{2-n}$ wherein Y is a sulfide polydentate ligand, X is a linear, branched, or cyclic alkoxy group, an amine, or a carboxylate ester, having 1 to 20 carbon atoms, wherein 1≤n≤2.

Sn(Y)(X) wherein Y is a sulfide tridentate ligand with the general formula $^-$SARA wherein R is a linear, branched or cyclic alkyl group having 1 to 20 carbon atoms and wherein A is S$^-$, O$^-$, or COO$^-$, X is a linear, branched or cyclic alkoxy, enoloxy, or carboxylate ester having 1 to 20 carbons atoms; a titanate compound selected from the formulae consisting of Ti(X) wherein X is a polydentate ligand with the general formula ARARARA wherein is a linear, branched or cyclic alkyl group having 1 to 20 carbon atoms and A is selected from N, O$^-$, or COO$^-$, and then elevating the temperature of the combination of the silicone composition containing the command cure catalyst to cure the combination.

DETAILED DESCRIPTION OF THE INVENTION

The present invention relates to modified or inhibited catalysts which provide an extended pot life and may be command cured such that the catalyst completely deactivates. This is accomplished by replacing the active ligands on conventional catalysts. Achieving such catalytic characteristics is achieved by replacing the reactive ligands on an existing catalyst with less labile groups to attenuate catalytic activity. Elevating the temperature raises the activity of the catalyst and removes the non-reactive ligands, freeing the catalyst to behave normally. "Elevating the temperature" for purposes of this invention means a minimum temperature of about 200° F is required to get a satisfactory cure of the composition. It is preferred to use higher temperatures in order to decrease the cure time, and temperatures on the order of about 350° F. to about 400° F. will suffice for a cure time of generally less than about 6 minutes.

One embodiment of this invention uses a form of the conventional condensation cure catalysts (tin or titanate compounds) but modifies the condensation cure catalyst such that it inhibits their reactivity to the degree that they can sit in fully formulated materials for long periods of time without showing catalytic activity, yet become very active when heated. These modified catalysts are unique because unmodified, these catalysts are very active catalysts and do not exhibit low catalytic activity so as to have, a long and useful pot life at room temperature.

These catalysts give a pot life of approximately 1 to 3 days once exposed to the atmosphere. If the composition is protected from moisture, then the pot life is somewhere in the range of about 6 months to a year, or longer.

The catalysts of this invention are used in concentrations of from about 0.05 weight % to about 3 weight % based on the total curable composition. Preferably, amount of about 1 weight % are used.

An embodiment of the present invention also advantageously produces a coating which is far more stable than conventional tin-catalyzed reactions. As described, conventional tin catalysts never deactivate, which can lead do unstable coatings which deteriorate in the presence of heat, fire or even weather. Such catalysts also remain biologically active and can pollute surrounding environment. By utilizing a tetravalent or divalent tin where every ligand is chemically active, the tin complex will eventually hydrolyze and self-condense to form tin oxide, which is mostly inert:

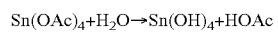

Sn(OAc)$_4$+H$_2$O→Sn(OH)$_4$+HOAc

Sn(OH)$_4$+Sn(OH)$_4$→SnO$_2$+H$_2$O

Such reactions demonstrate that leaving groups are used as part of the process to fully inactivate the catalyst. In this type of reaction, the non-active catalyst migrates to the surface of the polymer. This migration may contribute to the skin formation on the surface of the polymer, or may result in evaporation of the catalyst. In addition, prior to full evaporation of the catalyst, a dead catalyst may be reactivated through catalyst addition.

In another aspect of the present invention, to demonstrate both room temperature catalytic attenuation and the possible fugitive nature of the catalyst, two "command cure" tin catalysts were created: dibutyltinbis(mercaptopropyltrimethoxysilane) and tetra(mercapropropyltrimethoxysilane) tin.

These command cure catalysts are useful in coatings, for example, in roll coating, rotogravure, curtain coating, spray systems, screen printing, and in digital printing, and as catalysts for sealants for factory glazing.

A digital ink can be formulated from 40 parts of methoxy functional methylsilsesquioxane; 30 parts of methoxy terminated phenylmethylsiloxane; 25 parts of pigment, and 5 parts of triethoxyamine titanium.

A sealant can be formulated from 75.5 parts of 50,600 cPs silanol terminated polydimethylsiloxane; 4 parts of methyltris-(methylethylketoxime)silane; 20 parts of treated fumed silica and 0.5 parts of dibutyltin bis(dodecylmercaptide) and another sealant can be formulated from 51.5 parts of 50,000 cPs silanol terminated polydimethylsiloxane; 3 parts of tetraethylorthosilicate; 10 parts of treated fumed silica; 30 parts of treated precipitated CaCO$_3$; 5 parts of pigment, and 0.5 parts of dibutyltin bis(trimethoxysilyl-propylmercaptide).

EXAMPLES

Example 1

Dibutyltinbis(mercaptopropyltrimethoxysilane) (hereafter referred to as Command Cure Tin 1 or CC Tin 1) was created by reaction of dibutyltindiacetate (DBTDA) with mercaptopropyltrimethoxysilane in a 1:2 stoichiometric ratio. After mixing the reactants, the headspace was purged with nitrogen, gas and stored at 40 degrees Celsius for one hour. After storing, the mixture was placed into a vacuum chamber to a pressure of at least 0.5 in. Hg to boil the acetic acid from the mixture. Using a 5 cfm dual stage vacuum pump with a dry ice cold trap, the vacuum was held until all boiling ceased.

Example 2

Tetra(mercaptopropyltrimethoxysilane) tin (hereafter referred to as Command Cure Tin 2 or CC Tin 2) was created by reaction of tin(IV) acetate with mercaptopropyltrimethoxysilane in a 1:4 stoichiometric ratio. After mixing the reactants, the headspace was purged with nitrogen gas and stored at 40 degrees Celsius for one hour. After storing, the mixture was placed into a vacuum chamber to a pressure of at least 0.5 in Hg to boil out the acetic acid of the mixture. Then the vacuum is held until all boiling ceased.

CC Tin 1 and CC Tin 2 were compared to their unaltered originals, DBTDA and tin(IV) acetate, by addition to a standardized silanol resin system with the following formula: 50% silanol resin, 4% methyltrimethoxysilane (MTMS) 40% calcium carbonate, 5% TiO2 pigment, and 1% catalyst.

Example 3

After mixing the materials using a FlackTek DAC 400 FVZ Speed Mixer, each formula was applied to a glass sample at a thickness of 5 mils and allowed to sit open to the atmosphere at a temperature of 70° F., referred to as the "ambient" curing glass. Films of a thickness of about 10 mils or less are considered thin films, and are frequently used in the field of substrate coatings. A second glass sample at the same thickness was cured in an infrared oven at 350° F. for 6 minutes, While the remaining material was left in its container, with the lid off, open to the atmosphere at 70°F. A Shel Lab forced air oven was used for these steps.

The Ambient curing glass samples were checked for cure periodically by touching the surface for tackiness. Tackiness is determined by touching the sample surface with a gloved hand. If no imprint is left on the sample surface, nor any material transferred to the glove, the sample is tack free.

| Catalyst | Initial Infrared Cure | 5 mils Tack Free Time | Pot Life |
| --- | --- | --- | --- |
| DBTDA | Yes | <15 minutes | <10 minutes |
| CC Tin 1 | Yes | 72 hours | 24 hours skin over |
| Tin(IV) | Yes | <10 minutes | <10 minutes |
| CC Tin 2 | Yes | >10 days | >10 days |

The initial infrared cure tested whether the samples would cure immediately after the materials were applied to the glass. As the table shows, each of the four catalysts were successfully cured in the infrared oven, which is defined as when they were tack free.

CC Tin 1 changed the cure time from less than 15 minutes to 3 days at an applied thickness of 5 mils, demonstrating an increase in cure time of 28700%.

CC Tin 2 on the other hand, never cured in the time given. At the 10 day mark, the sample at 5 mils was still wet. It was then heated in the IR oven following the same curing procedure as before, yet. remained wet and uncured. A sample was taken from the container (which had been sitting at ambient temperature) and coated onto a glass slide at 5 mils thickness and also placed, into the IR oven. This failed to cure as well. To ensure that all the crosslinker had not merely evaporated, an additional 4% MTMS crosslinker was added to the formula, another 5 mils thick sample was created and placed into the IR oven. This sample also failed to cure.

It was concluded that CC Tin 1 and CC Tin 2 were successfully attenuated at room temperature while retaining their catalytic activity once heated to 350° F. for 6 minutes. CC Tin 2 loses all catalytic activity at both room temperature and elevated temperatures after a period of less than or equal to 10 days. Therefore, CC Tin 2 will cure if it is brought to elevated temperatures within a time frame between a few hours and ten days after it is exposed to moisture. It is surmised from the observations that the catalyst hydrolyses and condenses to form tin oxide.

An example of an inhibited titanate catalyst is titanium diglyceride bis(acetylacetonate) formed by first mixing titanium diisopropoxide bis(acetylacetonate) with glycerol in a 1:1 stoichiometric ratio. The mixing step was followed by purging the headspace with nitrogen gas and storing the mixture at 40 degrees Celsius for one hour. After storing, the mixture was placed in a vacuum chamber to a pressure of at least 3.5 in Hg to boil the isopropanol from the mixture. Then the vacuum was held until all boiling ceased.

Example 4

It is to foe noted that these catalysts can be used in conventional room temperature vulcanizing formulations. A typical formulation can be, for example, 80 parts of methoxy end-blocked polydimethyisiloxane having a viscosity of 2000 cPs; 5 parts treated fumed silica; 10 parts of treated precipitated $CaCO_3$; 4 parts of $TiO_2$ and 1 part of dibutyltin bis(trimethoxysilylpropylmercaptide).

This formula had a pot life of greater than 1 week at room temperature. A sample on a glass slide at 10 mils did not cure in greater than 1 week.

Example 5

In another formulation consisting of 60 parts of 50,000 cPs silanol end-blocked polydimethyisiloxane; 4 parts of tetraethyl orthosilicate; 5 parts of treated fumed silica 25 parts of treated precipitated $CaCO_3$; 4 parts of $TiO_2$, 1 part of Tetra-n-butyltitanate and 0.8 parts of triethanolamine. This formula had a pot life of greater than 19 hours and a 10 mil sample on a glass slide did not cure until about 48 hours.

A person skilled in the art would understand how to modify or inhibit other tin and titanate catalysts to perform similar modifications. Tin catalysts may be so inhibited by the use of hindered alcohols, mercaptans and chelates so that they do not react, or react very slowly, at room temperature and so that when they are heated to high temperatures, the chelates are dissipated and the catalysts become active and fast, reactions occur. Forms of the inhibited tin catalysts, when tin is divalent include: $Sn(OCnH_{2n+1})_2$, $Sn(Chelate)$, $Sn(SR)_2$, where R is a hydrocarbon. Such forms of the inhibited tin catalysts when tin is tetravalent include; $R_2Sn(OCnH_{2n+1})_2$ $R_2Sn$ (Chelate), $R_2Sn(SR)_2$, where R is a hydrocarbon monodentate ligand.

Titanate catalysts, when uninhabited, cause reactions quickly at room temperatures. Titanate catalysts can be inhibited so that they cure slowly at room temperature cure by the use of ligands similar to those used to inhibit tin catalysts. Examples of inhibited titanate catalysts are: $Ti(SR)_4$, $A_2Ti(SR)_2$, $RS_2Ti$ (Chelate), $RS_2Ti(Chelate)_2$, Ti(Chelate) where R is either a mono or polydentate hydrocarbon ligand and A is an alkoxy.

The following table demonstrates trials and results of various reactants. All reactants were obtained from Sigma Aldrich.

| | Reactant 1 | Reactant 2 | Tin/Titanate Complex | Cure attenuation? |
|---|---|---|---|---|
| Composition 1 | dibutyltindiacetate | Phenol | Tin Complex | None |
| Composition 2 | dibutyltindiacetate | t-butanol | Tin Complex | None |
| Composition 3 | dibutyltindiacetate | 3,5-dimethylhex-1-in-3-ol | Tin Complex | None |
| Composition 4 | dibutyltindiacetate | hexylene glycol | Tin Complex | None |
| CC Tin 1 | dibutyltindiacetate | mercaptopropyl-trimethoxysilane | dibutyltinbis-(mercaptoproyl-trimethoxysilane) | Yes |
| CC Tin 2 | tin(IV) acetate | mercaptopropyl-trimethoxysilane | tetra(mercaptopropyl-trimethoxysilane)tin | Yes |
| Composition 5 | titanium diisopropoxide bis(acetylacetonate) | mercaptopropyl-trimethoxysilane | Titanate Complex | Rate was 3x of unmodified precursor |
| Composition 6 | titanium tetra(n-butoxide) | mercaptopropyl-trimethoxysilane | Titanate Complex | None |
| Composition 7 | titanium tetra(n-butoxide) | Glycerol | Titanate Complex | Infinite |
| Composition 8 | titanium diisopropoxide bis(acetylacetonate) | Glycerol | titanium diglyceride bis(acetylacetonate) | Yes |

This table includes CC Tin 1, CC Tin 2 and Composition 8, which showed significant cure attenuation. The other compositions are those that were tested but did not successfully yield a command cure metal complex with satisfactory improvement in cure time. Composition 5 showed a cure rate that was approximately three times greater than that of the modified titanate precursor, titanium: diisopropoxide bis(acetylacetonate), however, this was deemed insufficient as the cure time was still approximately one hour, while the control had a cure rate of approximately 20 minutes. Also, the physical product of Composition 7 was a white solid that was soluble in isopropanol. Composition 7 showed infinite cure attenuation (no catalytic activity). This result was probably due to the solid complex not being in phase with the silicone.

The command cure system using the methods and catalysts disclosed, herein can offer reuse of static and dynamic mixing systems without clean-up. Also, this chemistry is particularly beneficial for thin films or thin pre-pregs because such inhibited catalysts allow for extended pre-preg shelf life and greatly reduce or eliminate the need for pre-preg refrigeration until use.

The reaction of such inhibited tin or titanate catalysts leads to products that eventually hydrolyze and self-condenses to a product which is mostly or completely inert. Such an inert or a catalyst which fully deactivates is beneficial because the end product, such as a glass coating, is much more resilient to external, damaging conditions including heat, water, and weather, in general. Therefore, after application, of a coating to architectural glass, for example, a user would be able to better rely on the longevity of the coating without repairs. In addition, such non-reactivity allows for improved storage and shelf life.

What is claimed is:

1. A composition of matter comprising (A.) a silicone composition that cures through silanol condensation reactions and (B.) a command cure catalyst, wherein said command cure catalyst is selected from the group comprising:
   a. a tin compound selected from the group of formulae consisting of:
      i. $Sn(Y)_n(X)_{4-n}$ wherein Y is a sulfide group with the general formula $RS^-$ is a linear, branched or cyclic alkyl group having 1 to 20 carbon atoms or an aryl group containing 6 to 20 carbon atoms, X is selected from an linear, branched, or cyclic alkoxy group, an enoloxy group, or a carboxylate ester having 1 to 20 carbon atoms, n has a value of 1, 2, 3, or 4, and $1 \leq n \leq 4$;
      ii. $Sn(Y)_n(X)_{2-n}$ wherein Y is a sulfide polydentate ligand, X is a linear, branched, or cyclic alkoxy group, an amine, or a carboxylate ester, having 1 to 20 carbon atoms, wherein $1 \leq n \leq 2$;
      iii. $Sn(Y)(X)$ wherein Y is a sulfide tridentate ligand with the general formula $^-SARA$ wherein R is a linear, branched or cyclic alkyl group having 1 to 20 carbon atoms and wherein A is $S^-, O^-,$ or $COO^-$, X is a linear, branched or cyclic alkoxy, enoloxy, or carboxylate ester having 1 to 20 carbons atoms;
   b. a titanate compound selected from the formulae consisting of:
      i. $Ti(X)_n$ wherein X is a polydentate ligand with the general formula ARARARA wherein R is a linear, branched or cyclic alkyl group having 1 to 20 carbon atoms and A is selected from N, $O^-$, or $COO^-$.

2. A composition of matter as claimed in claim 1 wherein the command cure catalyst is dibutyltin bis-(trimethoxysilyl mercaptide).

3. A composition of matter as claimed in claim 1 wherein the command cure catalyst is triethoxyamine titanium.

4. A composition of matter as claimed in claim 1 that is:
   a. 65 parts methoxy end block polydimethylsiloxane having a viscosity of 2000 cPs;
   b. 10 parts of treated fumed silica;
   c. 20 parts of treated precipitated calcium carbonate;
   d. 4 parts pigment, and,
   e. 1 part of dibutyltin bis(trimethoxysilylpropyl mercaptide).

5. A composition of matter as claimed in claim 1 that is:
   a. 65 parts methoxy end block polydimethylsiloxane having a viscosity of 2000 cPs;
   b. 10 parts of treated fumed silica;

c. 20 parts of treated precipitated calcium carbonate;
d. 4 parts pigment, and,
e. 1 part of dibutyltin bis(dodecylmercaptide).

6. A composition of matter as claimed in claim 1 that is:
a. 65 parts methoxy end block polydimethylsiloxane having a viscosity of 2000 cPs;
b. 10 parts of treated fumed silica;
c. 20 parts of treated precipitated calcium carbonate;
d. 4 parts pigment, and,
e. 1 part of triethoxyamine titanium.

\* \* \* \* \*